(12) United States Patent
Collins

(10) Patent No.: US 10,783,225 B1
(45) Date of Patent: Sep. 22, 2020

(54) METHOD AND SYSTEM FOR DRUG SCREENING

(71) Applicant: Blair Richard Collins, Somerville, MA (US)

(72) Inventor: Blair Richard Collins, Somerville, MA (US)

( * ) Notice: Subject to any disclaimer, the term of this patent is extended or adjusted under 35 U.S.C. 154(b) by 0 days.

(21) Appl. No.: 15/263,062

(22) Filed: Aug. 28, 2016

Related U.S. Application Data

(60) Provisional application No. 62/211,529, filed on Aug. 28, 2015.

(51) Int. Cl.
| | |
|---|---|
| *G05B 19/00* | (2006.01) |
| *G06F 21/32* | (2013.01) |
| *A61B 5/00* | (2006.01) |
| *G16H 10/60* | (2018.01) |
| *G07C 9/37* | (2020.01) |

(52) U.S. Cl.
CPC .......... *G06F 21/32* (2013.01); *A61B 5/4845* (2013.01); *G07C 9/37* (2020.01); *G16H 10/60* (2018.01)

(58) Field of Classification Search
CPC ... G06F 21/32; G06F 19/322; G07C 9/00158; A61B 5/4845
USPC .......................................................... 340/5.83
See application file for complete search history.

(56) References Cited

U.S. PATENT DOCUMENTS

| | | | | |
|---|---|---|---|---|
| 9,202,026 | B1* | 12/2015 | Reeves | G06F 21/30 |
| 9,426,139 | B1* | 8/2016 | McClintock | H04L 63/08 |
| 9,736,652 | B2* | 8/2017 | Su | H04W 4/028 |
| 2002/0150282 | A1* | 10/2002 | Kinsella | G06F 21/32 382/124 |
| 2013/0328664 | A1* | 12/2013 | Torgersrud | G07C 9/00031 340/5.83 |
| 2014/0031730 | A1* | 1/2014 | Hornbach | A61H 7/00 601/148 |
| 2015/0099946 | A1* | 4/2015 | Sahin | A61B 5/16 600/301 |
| 2016/0044228 | A1* | 2/2016 | Kim | H04N 5/2258 348/345 |

\* cited by examiner

*Primary Examiner* — Dhaval V Patel
(74) *Attorney, Agent, or Firm* — William Mansfield

(57) ABSTRACT

A computer-implemented method and system for connecting remote users with data gathered from a variety of apparatus: surveillance apparatus, identity confirmation apparatus, and drug testing apparatus to allow said remote users to know who is attempting to enter a given facility, whether a given person attempting entry to a given facility has or has not failed one or more drug tests, and what activity, such as drug use, is occurring at a given facility.

20 Claims, 6 Drawing Sheets

METHOD AND SYSTEM FOR DRUG SCREENING

STATEMENT REGARDING FEDERALLY SPONSORED RESEARCH OR DEVELOPMENT

Not Applicable.

CROSS-REFERENCE TO RELATED APPLICATIONS

Not Applicable.

TECHNICAL FIELD

The present invention relates generally to the fields of drug testing, surveillance, and identity confirmation.

BACKGROUND

There has been a long-felt need for more effective means of supporting addicted persons in their recovery using drug testing with some means to know the right persons are being tested and only the right persons are being allowed into recovery facilities and that drugs are not being brought into recovery facilities. Despite many attempts no highly-effective system has yet been developed. The current state of the art relies on guards who must be present on-site.

SUMMARY OF THE INVENTION

In general, in an aspect, the present invention comprises a computer-based method and system for coordinating the use of three types of apparatus, namely surveillance apparatus, identity verification apparatus, and drug testing apparatus. This computer-based method could, in one embodiment, utilize the Internet as a means for transmitting information gathered by the apparatus. One purpose of the method and system would be to verify who enters a facility, to drug test all persons attempting to enter a facility and to deny entry to all persons who fail the drug tests, and finally to conduct surveillance of all activities in a facility, such as a sober house. In one embodiment, the computer-based method could include use of an optical scanner as a means of detecting substance, i.e., alcohol or illegal drug, use.

In general, in an aspect, a system comprising one or more processors or virtual machines, one or more memory units, one or more input devices and one or more output devices, a network, and shared memory supporting communication among the processors, for connecting persons monitoring a drug recovery facility to ensure that no drugs are brought into the facility, no persons who fail drug tests are allowed in the facility, and to ensure that only authenticated users of the facility can enter the facility.

In general, in an aspect, a machine-based method for connecting persons remote from a drug recovery facility with activity there so that the identity of all persons attempting to enter that facility can be ascertained, all persons attempting to enter that facility can be drug tested, and such that all activity at that facility can be remotely monitored to detect the presence of contraband.

In general, in another aspect, a non-transitory computer readable medium for remotely monitoring a drug recovery facility, such as a sober house, to ensure that only authenticated persons, not on drugs, and not carrying drugs can enter said facility. The method and system would integrate control of surveillance means, identity confirmation means, and drug testing means. These means could be integrated into a mobile phone application, a desktop application, and other software applications to facilitate verification of the identity of persons attempting to enter the drug recovery facility, to facilitate drug testing of those persons, and to facilitate monitoring of the activity of those persons for the purpose of denying entry into the drug recovery facility of persons who fail drug tests, are not authenticated users of the drug recovery facility, and to deny entry to those carrying drugs and to assist in catching those using drugs at drug recovery facilities.

Some or all of the above needs may be addressed by certain embodiments of the invention. Certain embodiments of the invention may include systems and methods for fostering monitoring of multiple drug recovery facilities. The present invention overcomes the limitations of conventional approaches by providing, in a secure online environment, information to remote users related to who is attempting to enter a facility, the status of those persons, i.e. did they fail one or more drug tests, and what activities are occurring at those facilities. Aspects and advantages of the invention will be set forth in part in the following description, or may be obvious from the description, or may be learned through practice of the invention.

Variations and modifications can be made to these exemplary embodiments of the present disclosure. Other embodiments and aspects of the invention are described in detail herein and are considered a part of the claimed invention. Such other embodiments and aspects can be understood with reference to the following detailed description, accompanying drawings, and claims.

BRIEF DESCRIPTION OF THE FIGURES

A full and enabling disclosure of the present invention, including the best mode thereof, directed to one of ordinary skill in the art, is set forth in the specification, which makes reference to the appended figures, which are not necessarily drawn to scale, and wherein.

DETAILED DESCRIPTION OF THE PREFERRED EMBODIMENT

Figure 1:
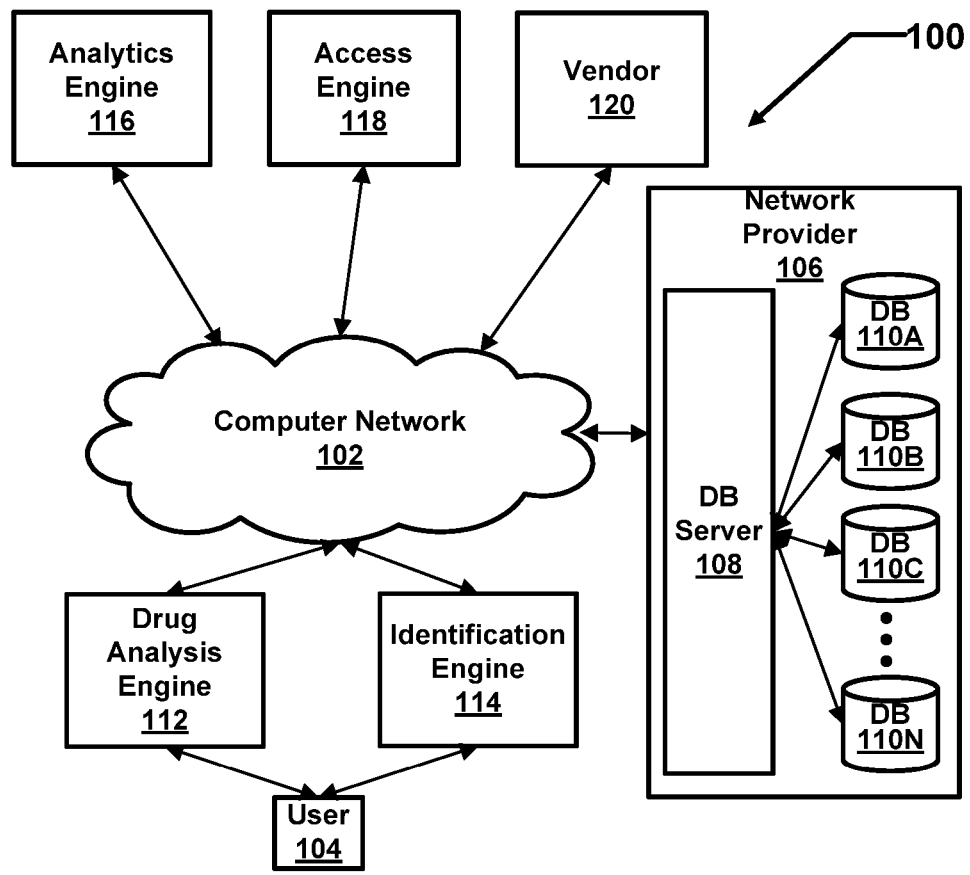
FIG. 1. Schematic Diagram of the Sensing/Security Network

Reference now will be made in detail to embodiments of the invention, one or more examples of which are illustrated more fully in the drawings. Each example is provided by way of explanation of the invention, not limitation of the invention. This invention may, however, be embodied in many different forms and should not be construed as limited to the embodiments set forth herein; rather, these embodiments are provided so that this disclosure will be thorough and complete, and will fully convey the scope of the invention to those skilled in the art. In fact, it will be apparent to those skilled in the art that various modifications and variations can be made in the present invention without departing from the scope or spirit of the invention. For instance, features illustrated or described as part of one embodiment can be used with another embodiment and such variations come within the scope of the appended claims and their equivalents.

Like numbers refer to like elements to those skilled in the art. Like numbers refer to like elements throughout. The term "exemplary" as used throughout this document is defined to mean "example." It will be appreciated that terms such as "left", "right", "top", "bottom", "inwardly", "outwardly", "front", "inner", "up", and "down" and other positional descriptive terms used herein below are used merely for ease of description and refer to the orientation of the components as shown in the Figures. It should be understood that any orientation of the elements described herein is within the scope of the present invention.

As desired, embodiments of the invention may include the authentication and access system with more or less of the components illustrated.

The invention is described above with reference to block and flow diagrams of systems, methods, apparatuses, and/or computer program products according to exemplary embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. It is understood that these computer-executable program instructions may be utilized to transmit information on who is attempting to enter a facility, who is doing what activity at said facility, and the drug-using status of persons attempting to enter said facility via the Internet. These computer program instructions may also be stored in a non-transitory computer-readable memory that can direct a computer or other programmable data processing apparatus to function in a particular manner, such that the instructions stored in the non-transitory computer-readable memory produce an article of manufacture including instruction means that implement one or more functions specified in the flow diagram block or blocks. As an example, embodiments of the invention may provide for a computer program product, comprising a non-transitory computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks. In one embodiment, a handheld device, such as a smartphone, could be used to deliver said computer program instructions. These computer-implemented processes could be virtualized in a cloud-based environment.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

While the invention has been described in connection with what is presently considered to be the most practical and various embodiments, it is to be understood that the invention is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation. In one embodiment the device for obtaining physiological measurements would be an optical scanner to detect a user's use of alcohol or illegal drugs.

FIG. 1 illustrates an exemplary environment, 100, for secure monitoring of drug-free individuals in a computer-based network for monitoring access to facilities. A computer network, 102, connects a network provider, 106, with user interfacing devices, 112 and 112, for obtaining biometric and physiological measures and digitally transmitting the data to the computer network, 102. A drug analysis engine facilitates under video observation physiological sampling from the user, 104, such as by obtaining saliva, analyzing the sample for the presence of one or more pharmacological substances determined by the protocol invoked and transmits the results to the network, 102. An identification engine facilitates biometric measuring of the user, 104, such as obtaining facial images, finger prints, iris scans or retinal scans and obtaining scans of documents such as driver registrations or passports, and the matching of these data against entries on a database to provide positive identification of the user, 104. An analytics engine, 116, facilitates authentication, determination of present and forecasted status of the user, 104. An access engine, 118, facilitates entry to a facility of an authenticated user, 104, who meets the required criteria. A vendor, 120, provides resources required by the several engines, (112, 114, 116, 118), the facility and user, 104, tested.

The network provider, 106, supplies a database server, 108, to the computer network, 102, wherein the database server has one or more databases, 110 [110A, 110B, . . . , 110M], for storing user profiles, drug protocols, questions, answers, and messages as well as the historical data of networked facilities together with information on vendors, and the logistics needed to facilitate commerce.

The system that we describe here enables members of a community or users of a network, for example, owners and managers of drug recovery facilities, to remotely monitor activities at their facilities and who is trying to enter their facilities and whether those persons are under the influence of drugs.

Implementations of the system need not be limited to networks of the kind known as social or need not all classes of users, but some implementations will be in the context of social networks or will be corporate or both. For convenience, we sometimes refer to the system in some examples as a collaborative ecosystem network, but we mean that phrase in a very broad sense to include, for example, any sort of network or grouping in which a community of users participates.

Figure 2:
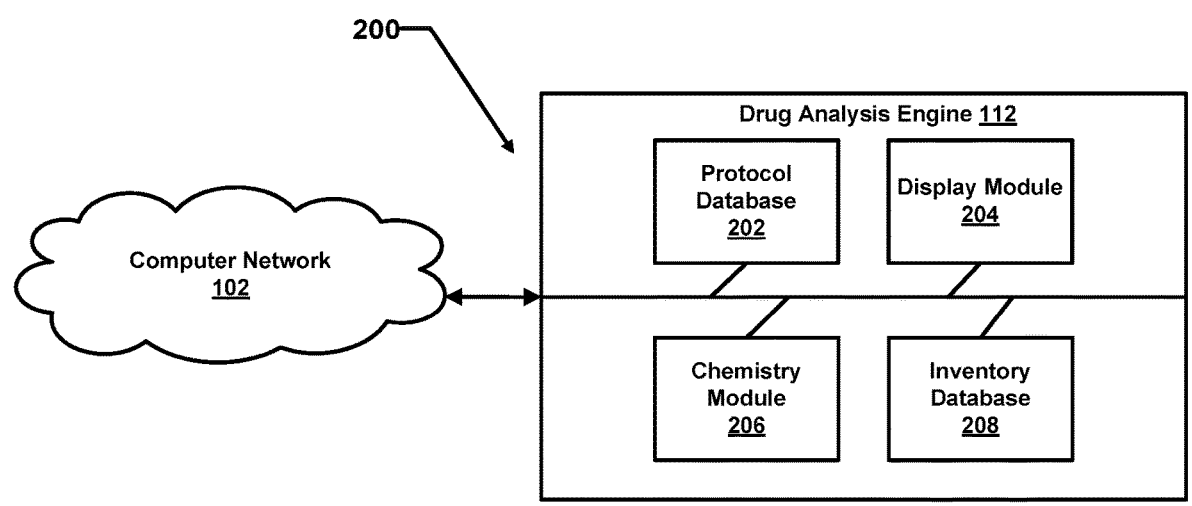
FIG. 2. Computer Block Diagram of Drug Analysis Engine

In the upcoming section reference is made to FIG. 2, a block diagram, 200, of an exemplary drug analysis engine, 112, which is included in the network environment, 100. The drug analysis engine, 112, in the network environment, 100, of FIG. 1, is configured with services for facilitating determination of the drug status of a user, 104, by analyzing physiological fluid samples. The drug analysis engine, 112, is further configured for secure sampling under video observation in the network environment, 100. The drug analysis engine, 112, comprises a protocol database, 202, a display module, 204, chemistry module, 206, together with the drug testing inventory database of historical data, 208. Said inventory database would include but not be limited to information on previous tests, previous users as well as information on the accuracy of each test. In some embodiments the drug testing engine's oral testing device is configured as described by Hartselle (U.S. Pat. No. 8,323,214, Oral testing devices and methods, granted Dec. 4, 2012) incorporated by reference in its entirety.

Figure 3:
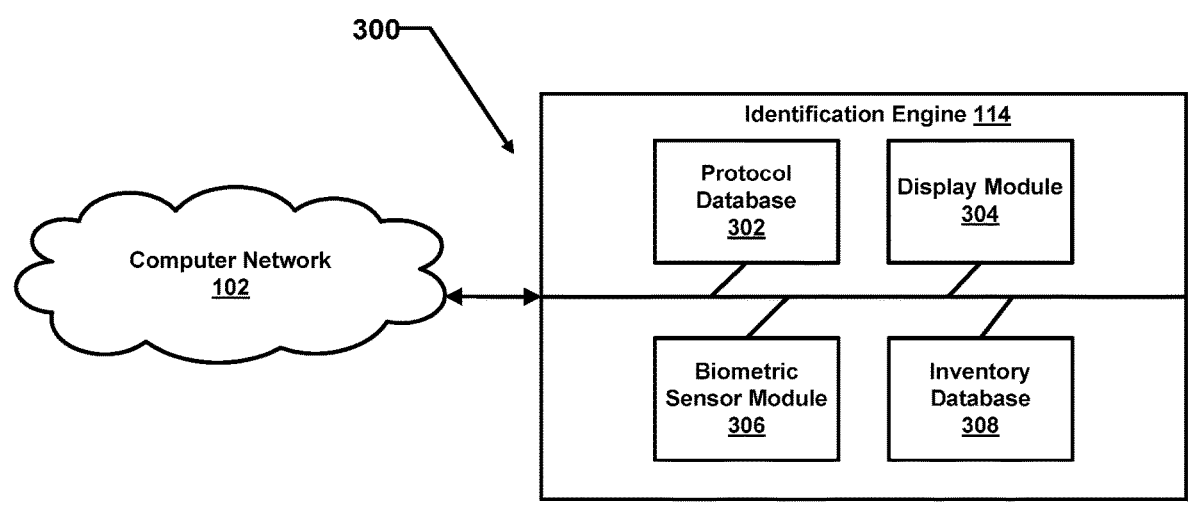
FIG. 3. Computer Block Diagram of Identification Engine

In the upcoming section reference is made to FIG. 3, a block diagram, 300, of an exemplary identification engine, 114, which is included in the collaborative network environment, 100. The identification engine, 114, in the network environment, 100, of FIG. 1, is configured with services for identifying user, 104, by using biometric measurements, scanned documents, and answers to queries. The identification engine, 114, is further configured for authentication of members under the agreement of the parties within the environment, 100. The identification engine, 114, comprises a protocol database, 302, a display module, 304, a biometric sensor module, 306, and having an inventory database of historical data, 308. Said inventory database would include but not be limited to information on biometric measurements in digital form such as fingerprints, voice prints, iris pattern, retinal pattern, facial image and scanned documents such as driver licenses, and passports. Using such historical data the user, 106, would be authenticated and the characteristics transmitted to the network, 100. In some embodiments the authentication would be made by a combination of various methods.

Figure 4:
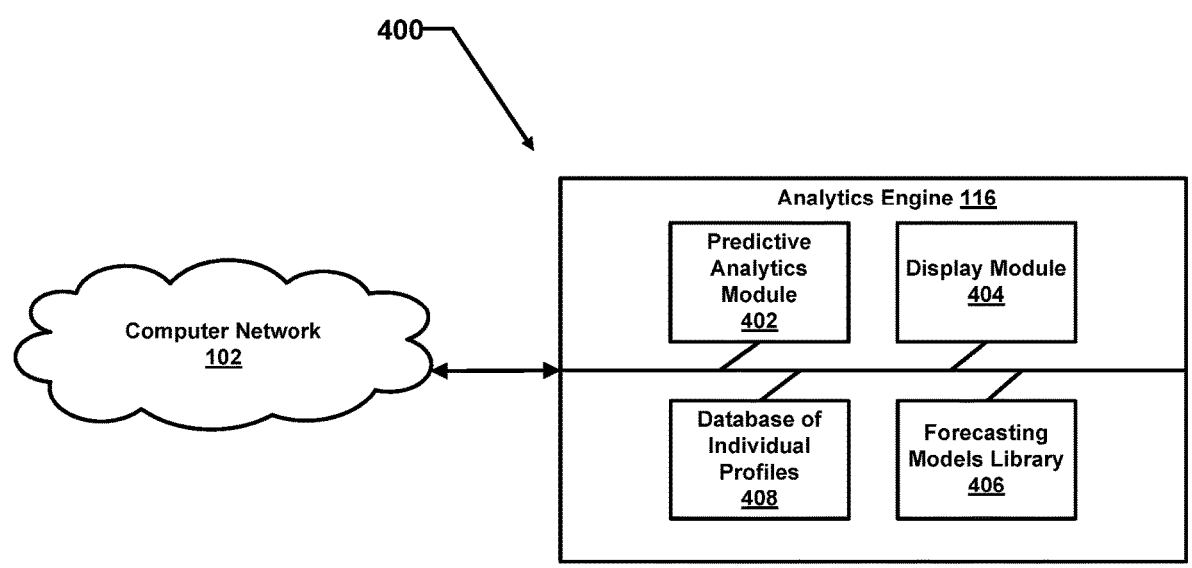
FIG. 4. Computer Block Diagram of Analytics Engine

In the upcoming section reference is made to FIG. 4, a block diagram, 400, of an analytic engine, 116. The network environment, 100, further includes an analytics engine, 116, that is configured with services for facilitating selection of users, 104, to review for deviant future behavior. A predictive analytics submodule, 402, applies search algorithms and forecasting models stored in the forecasting models library, 406, to the database of individual profiles, 408, to select individuals to scrutinize. The predictive analytics submodule, 402, may implement one or more forecasting techniques, including simple algorithms, including statistical techniques such as machine learning (e.g., as applied by IBM's Watson computer), game theory, and data mining. In some examples, the predictive analytics incorporate the robust, optimizing forecasting techniques of Pinto et al. (U.S. Pat. No. 7,499,897, issued on Mar. 3, 2009; U.S. Pat. No. 7,562,058, issued on Jul. 14, 2009; U.S. Pat. No. 7,725,300, issued on May 25, 2010; U.S. Pat. No. 7,730,003, issued on Jun. 1, 2010; U.S. Pat. No. 7,933,762, issued on Apr. 26, 2011; U.S. Pat. No. 8,170,841 issued on May 1, 2012; U.S. Pat. No. 8,751,273 issued on Jun. 10, 2014 and U.S. patent application Ser. No. 10/826,949, filed Apr. 16, 2004, the contents of all of which are incorporated herein by reference), that manage historical data including historical data that may have missing values, which must be inferred.

In some examples, the predictive analytics submodule, 402, may be configured as described by Gruber et al. (U.S. patent application Ser. No. 12/987,982, filed Jan. 10, 2011, and U.S. patent application Ser. No. 13/492,809 filed Jun. 9, 2012, the contents of both of which are incorporated herein by reference). For instance, the predictive analytics submodule, 402, may include an automated assistant receiving user input. The predictive analytics submodule, 402, may also include an active ontology with representations of concepts and relations among concepts drawn from various databases of historical data. The predictive analytics submodule, 402, may also include a language interpreter to parse the sender's input in order to derive a representation of the sender's intent in terms of the active ontology. The predictive analytics submodule, 402, may also include a services orchestration component to output responses and instructions to implement the sender's intent. A display module, 404, communicates the results of the analysis conducted by the predictive analytics submodule, 402, to the system observer.

In some examples, the predictive analytics submodule, 402, may have access to resume databases to analyze characteristics of potential drug recovery program cheaters, i.e., deviants. In some examples, the predictive analytics submodule, 402, may have access to a list of past or potential employers and may identify and rank potential deviants based on that list in terms of propensity to exhibit deviant behavior based on historical data. The predictive analytics submodule may develop a propensity score and may have as an input information about actions, feedback and background, for example, education level and training, job experiences, user or colleague feedback, measures of prior willingness to provide feedback, quality of prior responses or feedback, input from colleagues or other peers on character of possible deviants. Such propensity scores could be used, for example, as a differential outcome modifier. Using such historical data the predictive analytics of the analytical module could facilitate selection of the optimal persons to review.

Figure 5:
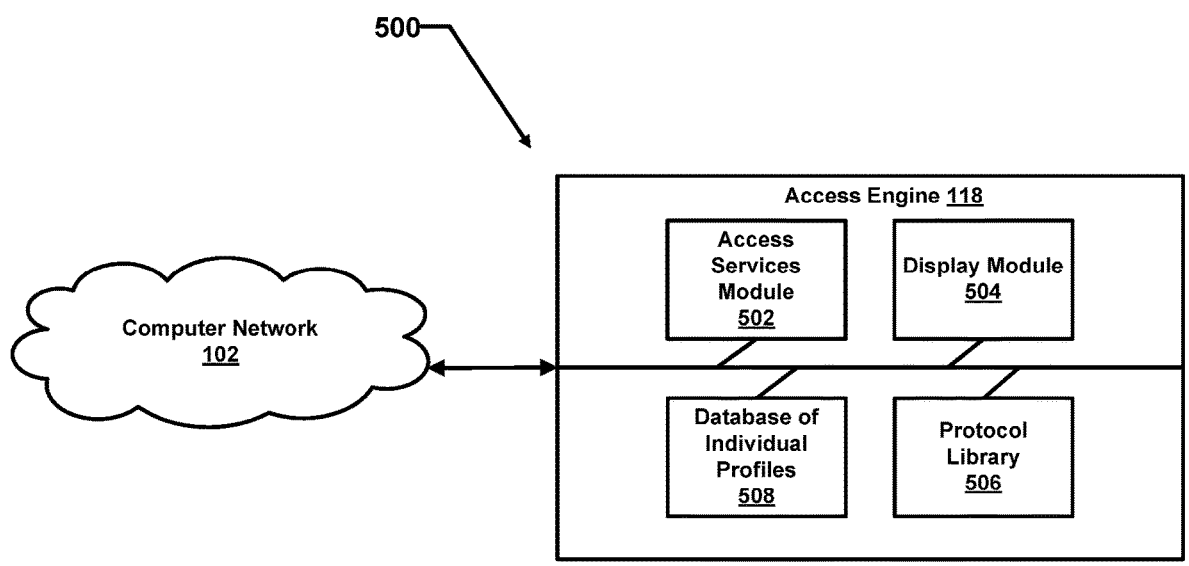
FIG. 5. Computer Block Diagram of Access Engine

In the upcoming section reference is made to FIG. 5. The network environment, 100, further includes an access engine, 118, that is configured with services for facilitating access to locations for authenticated individuals. The access engine, 118, comprises an access services module, 502, a display module, 504, a database of individual profiles, 506, and a protocol library, 508. The access services module, 502, upon confirming the authenticated identity of a user 106 (FIG. 1) in the profile library, 506, as determined by the identification engine 114 (FIG. 3) and the appropriate outcome from the drug testing engine 112 (FIG. 2) subject to the conditions of the analytic engine (FIG. 4) using the protocol specified in the database of individual profiles, 508, allows the user, 104, to enter the location which can be monitored on the display module, 504.

Figure 6:
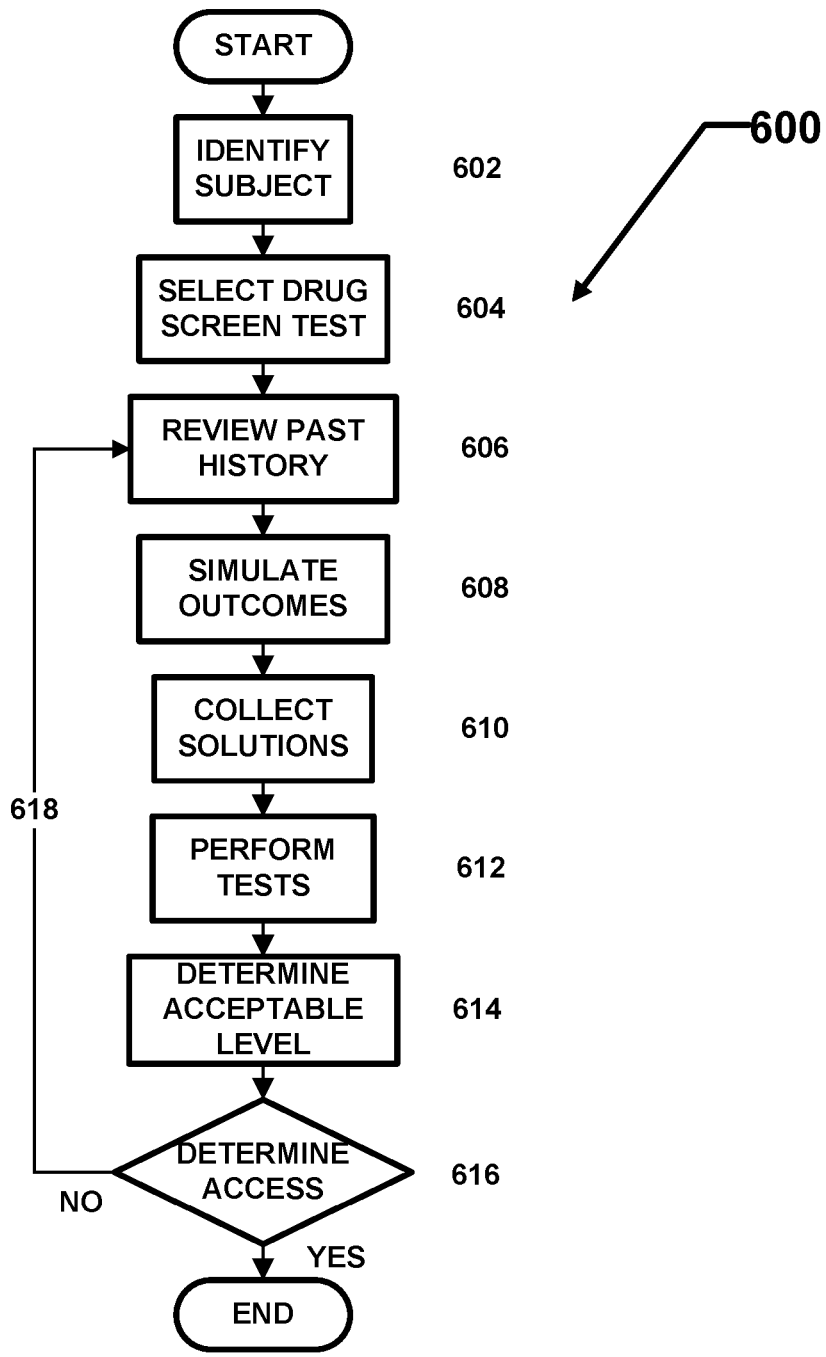
FIG. 6. Flowchart of Monitoring Path

In the upcoming section reference is made to FIG. 6, an exemplary sequence, 600, of secure access facilitated by the present invention, a registered user, 106, wants access to a location to which only authenticated users are allowed. The present invention performs the authentication in a series of steps.

Upon initiating the procedure identifying characteristics and documentation are obtained from the subject user, 106, in Step 602, using the identification engine, 114. Then the appropriate drug test is selected for the identified subject user, 106, in Step 604, using the drug testing engine, 114, informed by past history, 206. Then past history is reviewed, Step 606, and then possible outcomes are simulated in Step 608. Under video monitoring the appropriate solutions are collected in Step 610 and tests are performed by the chemistry module, 202, of the drug testing engine in Step 612. The collected drug levels are checked for acceptability in Step 614. Using the identification and the results of the drug testing along with the criteria assembled by the analytics engine, 116, at the choice point the access engine either grants access or does not, i.e., Step 616. If access is granted, the tested person can enter the facility. If access is not granted, the procedure reverts to Step 606 to review past history.

This written description uses examples to disclose the invention, including the best mode, and also to enable any person skilled in the art to practice the invention, including making and using any devices or systems and performing any incorporated methods. The patentable scope of the invention is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

While the invention has been described by reference to certain preferred embodiments, it should be understood that these embodiments are within the spirit and scope of the inventive concepts described. Accordingly, it is intended that the invention not be limited by the embodiments, but that it have the full scope permitted by the language of the following claims.

What is claimed is:

1. An apparatus comprising a non-transitory computer readable medium for remotely monitoring one or more drug recovery facilities, to ensure that only authenticated persons, not under the influence of alcohol or illegal drugs, and not carrying illegal drugs or alcohol can enter said one or more drug recovery facilities, said apparatus, controlled via a smartphone application, comprising identity verification means, taken from the group comprising video facial recognition or collected biometric measurements taken from the group comprising retinal scanning, fingerprinting, facial imaging or iris scanning, and comparison of documents presented by a user with authenticated documents previously presented by a user stored in a secure cloud-based database, drug testing means, comprising saliva-based testing, computer vision and machine learning applied to the results of the testing, and surveillance means further comprising one or more databases of historical authenticated documents and biometric measurements, video monitoring for facial recognition, means to detect specifics as to illegal drug, prescription drug, and alcohol use via said saliva-based testing means, means to control access to one or more facilities based on the results of the testing, and means to monitor users of the testing means who passed the tests and were allowed access to said one or more facilities via video monitoring of the motions and activities of all persons in said one or more facilities, including means for securely transmitting information as to which persons are inside said one or more facilities and what said persons are doing inside said one or more facilities so gathered to remote locations via use of the Internet and via SMS messages so that patterns are analyzed using predictive analytics and machine learning and so that a probability of recovery is assigned to each user of said apparatus.

2. The apparatus of claim 1 further comprising: a mobile phone application for displaying results of said identifying means, said drug testing means, and an analysis of said monitoring information comprising which users failed which drug or alcohol test at which moment in time, who is currently in the secured facility in real-time, which users passed the drug and alcohol test at which moment in time, and what are users are doing in said one or more facilities based on video monitoring of users' activities while inside said one or more facilities and further comprising a predictive analytics submodule for development of a propensity score of relapse as to each user of said apparatus based in part on input information about actions as to each user of said apparatus selected from the group comprising: education level and training, job experiences, user or colleague feedback, measurements of prior willingness of each user to provide feedback, quality of prior responses or feedback, input from colleagues or other peers on character of persons likely to relapse.

3. The apparatus of claim 1 further comprising identifying users via facial images obtained from video imagery to provide positive identification of the users by comparison to a secure cloud-based database containing known images of all the users of said apparatus.

4. The apparatus of claim 1 further comprising identifying users via fingerprints to provide positive identification of the users based on comparison of fingerprint data gathered in the past with currently gathered fingerprint data using a secure cloud-based database.

5. The apparatus of claim 1 further comprising identifying users via iris scans to provide positive identification of the users based on comparison of current iris scan data and previously gathered data using a secure cloud-based database.

6. The apparatus of claim 1 further comprising identifying users via retinal scans to provide positive identification of the users based on comparison of retinal scans obtained currently and previously obtained retinal scans using a secure cloud-based database.

7. The apparatus of claim 1 further comprising identifying users via obtaining historical scans of documents from the group comprising passports, driver license's, state identification cards, and other governmental identification cards and entering the data in a secure cloud-based database and obtaining current scans of said documents and matching this current data versus said historical entries in said secure cloud-based database to provide positive identification of the users.

8. The apparatus of claim 1 further comprising door locks operable to only unlock when a user passes a drug and alcohol test thus controlling access to said one or more facilities.

9. A system comprising a non-transitory computer readable medium and one or more processors, one or more memory units, one or more input devices, a network, and shared memory supporting communication among the processors for remotely monitoring one or more drug recovery facilities, to ensure that only authenticated persons, not under the influence of alcohol or illegal drugs, and not carrying illegal drugs can enter said one or more drug recovery facilities, said system, controlled via a smartphone application, comprising identity verification means, taken from the group comprising video facial recognition or collected biometric measurements taken from the group comprising retinal scanning, fingerprinting, facial imaging or iris scanning, and comparison of documents presented by a user with authenticated documents previously presented by a user stored in a secure cloud-based database, drug testing means, comprising saliva-based testing, computer vision and machine learning applied to the results of the testing, and surveillance means further comprising one or more databases of historical authenticated documents and biometric measurements, video monitoring for facial recognition, means to detect specifics as to illegal drug, prescription drug, and alcohol use via a saliva-based testing means, means to control access to one or more facilities based on the results of the testing, and means to monitor users of the testing means who passed the tests and were allowed access to said one or more facilities via video monitoring of the motion and activity of persons in said one or more facilities, including means for securely transmitting information as to which persons are inside said one or more facilities and what said persons are doing inside said one or more facilities so gathered to remote locations via use of the Internet and via SMS messages so that patterns are analyzed using predictive analytics and machine learning and so that a probability of recovery is assigned to each user of said system.

10. The system of claim 9 further comprising: a mobile phone application for displaying results of said identifying means, said drug testing means, and an analysis of said monitoring information comprising which users failed which drug or alcohol test at which moment in time, who is currently in the secured facility in real-time, which users passed the drug and alcohol test at which moment in time, and what are users doing in the facility based on video monitoring of users' activities while inside said one or more facilities and further comprising a predictive analytics submodule for development of a propensity score of relapse as to each user of said system based in part on input information about actions as to each user of said apparatus selected from the group comprising: education level and training, job experiences, user or colleague feedback, measurements of prior willingness of each user to provide feedback, quality of prior responses or feedback, input from colleagues or other peers on character of persons likely to relapse.

11. The system of claim 9 further comprising an analytics engine configured with services for selecting users to review for future relapse behavior based on predictive analytics and machine learning of trends and patterns in the data gathered on said users.

12. The system of claim 9 further comprising identifying users via facial images from obtained from video imagery to provide positive identification of the users by comparison to a secure cloud-based database containing known images of all the users of said system.

13. The system of claim 9 further comprising identifying users via fingerprints to provide positive identification of the user via comparison of current data to authenticated historical data located in a secure cloud-based database containing known images of all the users of said system.

14. The system of claim 9 further comprising identifying users via iris scans to provide positive identification of the users via comparison of current data to authenticated historical data located in a secure cloud-based database containing known images of all the users of said system.

15. The system of claim 9 further comprising identifying users via retinal scans to provide positive identification of the users via comparison of current data to authenticated historical data located in a secure cloud-based database containing known images of all the users of said system.

16. The system of claim 9 further comprising identifying users via obtaining historical scans of documents from the group comprising passports, driver license's, state identification cards, and other governmental identification cards and entering the data in a secure cloud-based database and obtaining current scans of said documents and matching this current data versus historical entries in said secure cloud-based database to provide positive identification of the users.

17. The system of claim 9 further comprising door locks operable to only unlock when a user passes a drug and alcohol test thus controlling access to one or more facilities.

18. A method for verifying the identity of persons, confirming if persons are under the influence of prescription drugs, illegal drugs or alcohol, and, if so, which drugs, and for monitoring the activity of persons at a facility; said method comprising of
  (a) identifying persons, including using one or more biometric measurements from the group comprising retinal scanning, fingerprinting, facial imaging using video imagery, iris scanning, and matching data from document to database entries;
  (b) detecting prescription drug, alcohol and illegal drug use by the persons identified in step a and which specific substances were being used by a user via an automatic analysis of a saliva test using computer vision and machine learning;
  (c) monitoring the motion and activity of persons, previously identified in step a and drug-tested in step b, in a facility via video monitoring, including means for transmitting info, as to activity of persons admitted to said facility previously identified in step a and drug-tested in step b, so gathered to remote locations via use of the Internet and via SMS messages, and analyzing said information via predictive analytics and machine learning.

19. The method of claim 17 further comprising a database server with one or more databases for
  (a) storing user profiles, drug protocols, questions, answers, messages, historical data from networked facilities, and vendor information for use in comparisons to real-time, currently obtained data.

20. The method of claim 17 further comprising a predictive analytics submodule
  (b) using search algorithms and forecasting models to select users to review in detail based on all data obtained related to the users; and
  (c) one or more forecasting techniques selected from the group comprising simple algorithms, machine learning, game theory, and data mining based on all data obtained related to the users.

* * * * *